United States Patent
Li et al.

(10) Patent No.: US 9,990,545 B2
(45) Date of Patent: Jun. 5, 2018

(54) EXTRACTION METHOD AND EXTRACTION DEVICE FOR CRIME SCENE FOOTPRINT THROUGH PHOTOGRAPHING

(71) Applicant: DALIAN EVERSPRY SCI & TECH CO., LTD, Dalian (CN)

(72) Inventors: Bo Li, Dalian (CN); Chongjian Tan, Dalian (CN)

(73) Assignee: DALIAN EVERSPRY SCI & TECH CO., LTD, Dalian (CN)

( * ) Notice: Subject to any disclaimer, the term of this patent is extended or adjusted under 35 U.S.C. 154(b) by 0 days. days.

(21) Appl. No.: 15/187,755

(22) Filed: Jun. 20, 2016

(65) Prior Publication Data

US 2016/0292508 A1 Oct. 6, 2016

Related U.S. Application Data

(63) Continuation of application No. PCT/CN2015/071926, filed on Jan. 30, 2015.

(30) Foreign Application Priority Data

Mar. 27, 2014 (CN) .......................... 2014 1 0116889
Mar. 27, 2014 (CN) .......................... 2014 1 0117440

(51) Int. Cl.
  *G06K 9/00* (2006.01)
  *G06T 5/00* (2006.01)
  (Continued)

(52) U.S. Cl.
  CPC ..... *G06K 9/00671* (2013.01); *G06K 9/00885* (2013.01); *G06K 9/2036* (2013.01);
  (Continued)

(58) Field of Classification Search
  CPC .. G06K 9/00067; G06K 9/0008; G06K 9/001; G06K 9/00073; G06K 9/00006; G06K 9/00744
  See application file for complete search history.

(56) References Cited

U.S. PATENT DOCUMENTS

2007/0280513 A1   12/2007  Engheta et al.
2011/0235871 A1*   9/2011  Byren ................ G06K 9/00033
                                                              382/124

(Continued)

FOREIGN PATENT DOCUMENTS

CN       103886601 A       6/2014
JP       2007226756 A      9/2007

*Primary Examiner* — Kenny Cese
(74) *Attorney, Agent, or Firm* — Perkins Coie LLP

(57) ABSTRACT

This application involves a crime scene footprint photography and extraction method and extraction device that can photograph a first image of the footprint in the oblique light from a fixed angle, and a second image of the footprint in the diffuse reflected light from a fixed angle; divide the first image's brightness component V1 by the second image's brightness component V2 to produce their brightness distribution ratio V3; and extract a third image corresponding to the brightness distribution ratio V3. According to the technical scheme of this application, the technology has a better image collection effect, and can provide better image materials for future footprint acquisition and identification, and can also remove the patterns of the footprint trace carrier, and leave only footprint images displayed clearly and cognizably. Moreover, the method is simple and the results are more accurate.

11 Claims, 4 Drawing Sheets

| | |
|---|---|
| Exposing under an oblique light source, and photographing a part ofor an entire illuminated area of said oblique light source from a fixed angle to obtain a first image, said first image contains a part of or an entire image of a footprint and a trace carrier image of said footprint | S1 |
| Exposing under a diffuse reflected light source, and photographing a part of or an entire illuminated area of said diffuse reflected light source from a fixed angle to obtain a second image, said second image contains animage of said trace carrier without any footprints | S2 |
| Analyzing said first image's brightness component Vi and said second image's brightness component V2, and divide said first image's brightness component Vi by said second image's brightness componentV2 to produce their brightness distribution ratio V3 | S3 |
| Extracting a third image corresponding to said brightness distribution ratio V3, said third image only contains an image of said footprint | S4 |

(51) Int. Cl.
*G06T 5/50* (2006.01)
*G06K 9/46* (2006.01)
*G06K 9/20* (2006.01)
*A61B 5/1174* (2016.01)

(52) U.S. Cl.
CPC ............ *G06K 9/4661* (2013.01); *G06T 5/009* (2013.01); *G06T 5/50* (2013.01); *A61B 5/1174* (2013.01); *G06T 2207/10152* (2013.01); *G06T 2207/20221* (2013.01)

(56) References Cited

U.S. PATENT DOCUMENTS

2013/0259331 A1* 10/2013 Maurer .............. G06K 9/00067
382/125
2015/0199996 A1* 7/2015 Krishnamurthy .. G11B 27/3081
386/241

* cited by examiner

| | |
|---|---|
| Exposing under an oblique light source, and photographing a part ofor an entire illuminated area of said oblique light source from a fixed angle to obtain a first image, said first image contains a part of or an entire image of a footprint and a trace carrier image of said footprint | S1 |
| Exposing under a diffuse reflected light source, and photographing a part of or an entire illuminated area of said diffuse reflected light source from a fixed angle to obtain a second image, said second image contains animage of said trace carrier without any footprints | S2 |
| Analyzing said first image's brightness component Vi and said second image's brightness component V2, and divide said first image's brightness component Vi by said second image's brightness componentV2 to produce their brightness distribution ratio V3 | S3 |
| Extracting a third image corresponding to said brightness distribution ratio V3, said third image only contains an image of said footprint | S4 |

Figure 1

| A first extraction module | 51 |
| :---: | :---: |
| A second extraction module | 52 |
| An analysis module | 53 |
| An extraction module | 54 |

Figure 5

EXTRACTION METHOD AND EXTRACTION DEVICE FOR CRIME SCENE FOOTPRINT THROUGH PHOTOGRAPHING

CROSS REFERENCE TO RELATED APPLICATIONS

This application is a continuation of PCT/CN2015/071926 filed Jan. 30, 2015, which claims priority to CN 201410116889.X filed Mar. 27, 2014 and CN 201410117440.5 filed Mar. 27, 2014, all of which are incorporated herein by reference.

FIELD OF TECHNOLOGY

This application involves the field of data collection and extraction technology, and particularly a crimescene footprint photography and extraction method and extraction device.

BACKGROUND TECHNOLOGY

Nowadays, when extracting common indoor footprint images on hard and flat ground, such as floor tiles and ground tiles, or a table surface, people still use the traditional manual operation methods with cameras and lights. There is still not an integrated portable device designed for the specific purpose of extracting footprints. Also, the present method of crime-scene footprint photography and extraction methods mainly utilize police floodlights from different angles and cameras to collect footprint images twice. The images collected for the first time show the footprint and its trace carrier, while those collected for the second time show the trace carrier without a footprint. Because all of the images have to be photographed manually on the scene, and the images vary when taken by different operators; there are common problems such as follows:

1. Tilted photographing angle causes the deformation of photographed footprint images;
2. The normal indoor lighting on the scene also makes the images of floor patterns clear, which interferes with effective footprint imaging;
3. Because manually operated by operators, the footprint image area has to be photographed with cameras at least twice, it is hard to photograph the images twice from exactly the same location. All of the abovementioned problems can interfere with the normal footprint image information, reduce the footprint image quality, and bring obstacles to recognition and analysis at a later stage.

The present application aims to overcome the shortcomings of the existing technology, and provides a crime-scene footprint photography and extraction method and extraction device.

The present application adopts the following technical schemes:

A crime-scene footprint image photography and extraction method includes the following steps:

S1: Exposing under an oblique light source, and photographing a part of or an entire illuminated area of said oblique light source from a fixed angle to obtain a first image, said first image contains a part of or an entire image of a footprint and a trace carrier image of said footprint;

S2: Exposing under a diffuse reflected light source, and photographing a part of or an entire illuminated area of said diffuse reflected light source from a fixed angle to obtain a second image, said second image contains an image of said trace carrier without any footprints;

S3: Analyzing said first image's brightness component V1 and said second image's brightness component V2, and divide said first image's brightness component V1 by said second image's brightness component V2 to produce their brightness distribution ratio V3;

S4: Extracting a third image corresponding to said brightness distribution ratio V3, said third image only contains an image of said footprint.

Preferred: Before said first image's brightness component V1 and said second image's brightness component V2 are obtained, converting said first image and said second image into HSV mode.

Preferred: In an oblique light illuminating environment, the intersection angle $\alpha$ between said oblique light and said footprint's trace carrier ranges between $0° \leq \alpha \leq 10°$.

Preferred: Said first image and said second image share the same photographing area.

Preferred: Said oblique light is formed from at least two light sources located on both sides along said footprint's width direction, said oblique light sources' length direction is consistent with said footprint's length direction; said oblique light sources can compensate each other to illuminate entire said footprint.

Preferred: Said oblique light sources that form said oblique light, are formed in a strip structure.

Preferred: Said oblique light sources that form said oblique light, are formed with collimating lens or the collimating lens system.

Preferred: In said diffuse reflected light source illuminating environment, said diffuse reflected light is emitted by area light sources, said diffuse reflected light is formed from at least two said area light sources, said two area light sources are located on both sides of said footprint's width direction and said two area light sources' length direction is consistent with said footprint's length direction.

Preferred: Said oblique light source and said diffuse reflected light source alternatively illuminate a photographing area.

Preferred: Said oblique light sources and said diffuse reflected light sources are formed from white light sources.

Preferred: Said intersection angle $\beta$ between a diffuse reflector used to form said diffuse reflected light and said trace carrier's surface ranges between $45° < \beta < 90°$.

A footprint image extraction device includes:

A first extraction module, is used to photograph a part of or an entire oblique light sources illuminated area to obtain a first image when exposed under said oblique light sources, said first image contains a part of or an entire image of a footprint, and an image of a trace carrier of said footprint;

A second extraction module, is used to photograph a part of or an entire diffuse reflected light sources illuminated area to obtain a second image, said second image contains an image of said trace carrier;

An analysis module, is used to analyze said first image's brightness component V1 and said second image's brightness component V2, and divide said first image's brightness component V1 by said second image's brightness component V2 to produce their brightness distribution ratio V3;

An extraction module, is used to extract a third image corresponding to said brightness distribution ratio V3, said third image only contains said footprint's image.

Preferred, including a conversion module, is used to convert said first image and said second image into HSV mode, before said first image's brightness component V1 and said second image's brightness component V2 are obtained.

Benefits from adopting the technical scheme of the present application are: The present application involves an on-scene footprint image photography and extraction method and extraction device that can photograph the image of a footprint and their trace carriers in the oblique light from a fixed angle, and in the diffuse reflected light environment, photograph the image of the trace carrier without the footprint from a fixed angle. The obtained two images can be compared and reduced to produce the footprint's image, Then removes the footprint trace carrier image, so as to display clear and cognizable footprint images only; Because the two images are photographed from the same location with the same angle, the footprint images obtained through calculation are more accurate. In addition, the on-scene footprint photography and extraction method provided in this application is simple, effective and rapid.

DESCRIPTION OF DRAWINGS

FIG. 1: Footprint image extraction method flow diagram based on an embodiment of the present application;

FIG. 5: Diagram of footprint image extraction device based on an embodiment of the present application.

DETAILED DESCRIPTION OF THE ILLUSTRATED EMBODIMENTS

Figure 2A:
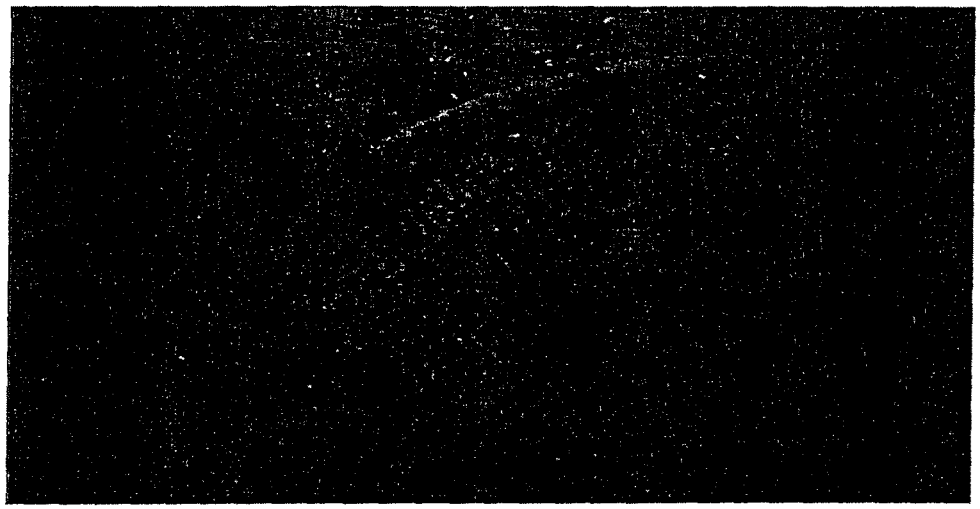
FIG. 2a: Schematic image photographed in the oblique light source based on an embodiment of the present application.

To better explain the abovementioned purposes, characteristics and advantages of this application, embodiments are illustrated in details combined with drawings as follows.

Detailed descriptions are provided below to help fully explain this application. Furthermore, this application can also be implemented in other ways. People in the art can promote similar method or device without deviating the connotation of this application. Therefore, this application is not restricted to the following embodiments.

Second, this application is specified in details on the basis of the drawings. For easy illustration, diagrams for the device structure are locally amplified in different proportions, and the abovementioned schematic diagrams are only examples, and they should not restrict the protection scope of this application. In addition, the actual production process shall involve three-dimensional sizes of length, width and depth.

According to the embodiments of this application, an on-scene footprint photography and extraction method and extraction device is provided.

As shown in FIG. 1, the extraction method includes:

S1: Exposing under an oblique light source, and photographing a part of or an entire illuminated area of said oblique light source from a fixed angle to obtain a first image, said first image contains a part of or an entire image of a footprint and a trace carrier image of said footprint;

S2: Exposing under a diffuse reflected light source, and photographing a part of or an entire illuminated area of said diffuse reflected light source from a fixed angle to obtain a second image, said second image contains an image of said trace carrier without any footprints;

S3: Analyzing said first image's brightness component V1 and said second image's brightness component V2, and divide said first image's brightness component V1 by said second image's brightness component V2 to produce their brightness distribution ratio V3;

S4: Extracting a third image corresponding to said brightness distribution ratio V3, said third image only contains an image of said footprint.

Specifically, equipment adopted to photograph on-scene footprints includes an equipment case, a camera, four groups of LED light sources, two groups of white LED side lights forming oblique light sources, and two groups of diffuse reflected light sources. The high pixel camera is fastened at the top of the case from a fixed angle, so as to standardize the footprint photography, and facilitate retrieval and identification at a later stage. In each extraction, the footprint is photographed respectively under oblique light and diffuse reflected light to obtain two sets of images to form images under different light sources, in order to facilitate background removal for footprint identification.

Preferred: The intersection angle α between the oblique light and the footprint's trace carrier ranges between $0°≤α≤10°$. The intersection angle within this range can achieve a better photographing effect, and the oblique light is formed from at least two light sources, which are respectively emitted on both sides of the footprint width direction, and the light sources' length direction is consistent with the footprint length direction.

Specifically, oblique light sources are set on both sides of the equipment case face-to-face, the equipment case is open at the bottom. When photographing, the equipment case shall be placed above the footprint that needed to be photographed, and place the oblique light sources on both sides of the footprint along the footprint's width direction, and the light source's length direction is consistent with the footprint's length direction. The oblique light shall be emitted within the target area, and the oblique lights on both sides of the footprint can be compensated to each other so as to illuminate the entire footprint. The target area refers to the area of the footprint and its trace carrier covered by the equipment case.

The oblique light sources that form the oblique light, are formed in a strip structure, and are formed with collimating lens or the collimating lens system. Collimating lens can be cylindrical lens, convex lens or concave reflectors, and the collimating lens system can be a combined structure of cylindrical lens, convex lens or concave reflectors. Cylindrical lens are chosen in the present embodiment.

The oblique light shall be emitted within the target area, and the oblique lights on both sides of the footprint can be compensated to each other so as to illuminate the entire footprint. Because the footprint's width is less than its length and the light attenuates as the emission distance increases, and therefore, the oblique light sources forming the oblique light are located on both sides of the footprint along the footprint's width direction, and the light source's length direction is consistent with the footprint's length direction. In other words, the oblique light sources are placed on both sides of the footprint's width direction, and emitted from one side of the footprint to the other side along the footprint's width direction. In doing so, the oblique light sources can compensate each other and avoid the inadequate illumination of the footprint between the two oblique light sources. If the two oblique light sources are placed at the toe and heel of the footprint, namely on both sides of the footprint's length direction, because the footprint's length direction is longer, the oblique light may attenuate excessively, which causes inadequate illumination of the footprint. In other embodiments, the oblique light sources can be placed at both sides of the footprint's width direction according to the photographing demands, and additional oblique light sources can be placed at both sides of the footprint's length direction to enhance the intensity of light in order to further improve photographing effect.

Preferred: In a diffuse reflected light illumination environment, area light sources are adopted to form a diffuse reflected light. The area light sources are placed at both sides of the footprint's width direction, and the light sources' length direction is consistent with the footprint's length direction. The trace carrier without any footprints, photographed in the diffuse reflected light illumination environment from a fixed angle, is a background image. Two footprint images can be photographed respectively in the oblique light and diffuse reflected light for the use of layer reduction and comparison to obtain the image of the footprint. Using those two footprint images and removing the background, the footprint's image can be obtained.

Both of the oblique light sources and diffuse reflected light sources are white light sources, and it is because white lights have shorter wavelengths and therefore have a better imaging effect.

The diffuse reflected light is provided by area light sources, lights emitted from LED hit a rough surface reflection plate and then diffuse to illuminate the footprint and its trace carrier. The diffuse reflected light sources are placed at both sides of the equipment case face-to-face and over the oblique light sources. In the present embodiment, the diffuse reflected light sources are placed on both sides of the footprint's width direction.

Multiple high pixel cameras are placed on the top of the equipment case, and vertically downward photograph the footprint and its trace carrier. In the present embodiment, two cameras are adopted and placed in the footprint's length direction.

Figure 2B:
FIG. 2b: Schematic image with an intercepted part photographed in the oblique light source based on an embodiment of the present application.

In the present embodiment, as shown in FIG. 2a, the image is photographed under oblique light sources, and said image contains patterns of both the footprint and its trace carrier. Because the image has many matrix elements in a brightness analysis, a part of the image is taken for an example to express the image's brightness components clearly. As shown in FIG. 2b, 2b1 shows the intercepted part of the image, and Table 1 shows brightness components extraction results:

TABLE 1

|    | 1      | 2      | 3      | 4      | 5      | 6      | 7      | 8      |
|----|--------|--------|--------|--------|--------|--------|--------|--------|
| 1  | 0.1725 | 0.1843 | 0.1804 | 0.1765 | 0.1804 | 0.1725 | 0.1686 | 0.1647 |
| 2  | 0.1922 | 0.1843 | 0.1843 | 0.1848 | 0.1882 | 0.1804 | 0.1725 | 0.1765 |
| 3  | 0.2039 | 0.1961 | 0.2000 | 0.2039 | 0.2000 | 0.1882 | 0.1843 | 0.1882 |
| 4  | 0.2078 | 0.2078 | 0.2118 | 0.2078 | 0.2039 | 0.2039 | 0.2000 | 0.1961 |
| 5  | 0.2118 | 0.2118 | 0.2157 | 0.2157 | 0.2118 | 0.2118 | 0.2078 | 0.2039 |
| 6  | 0.2118 | 0.2157 | 0.2235 | 0.2235 | 0.2235 | 0.2235 | 0.2196 | 0.2118 |
| 7  | 0.2196 | 0.2235 | 0.2196 | 0.2235 | 0.2235 | 0.2235 | 0.2196 | 0.2157 |
| 8  | 0.2157 | 0.2157 | 0.2118 | 0.2196 | 0.2235 | 0.2235 | 0.2196 | 0.2157 |
| 9  | 0.2039 | 0.2078 | 0.2039 | 0.2118 | 0.2196 | 0.2196 | 0.2235 | 0.2235 |
| 10 | 0.2078 | 0.2078 | 0.2039 | 0.2118 | 0.2196 | 0.2157 | 0.2196 | 0.2275 |
| 11 | 0.2000 | 0.2000 | 0.2078 | 0.2157 | 0.2196 | 0.2157 | 0.2157 | 0.2235 |
| 12 | 0.1922 | 0.1961 | 0.2039 | 0.2039 | 0.2078 | 0.2078 | 0.2078 | 0.2118 |
| 13 | 0.1765 | 0.1804 | 0.1882 | 0.1882 | 0.1882 | 0.1882 | 0.1882 | 0.1922 |
| 14 | 0.1647 | 0.1647 | 0.1727 | 0.1725 | 0.1725 | 0.1765 | 0.1765 | 0.1804 |
| 15 | 0.1451 | 0.1451 | 0.1490 | 0.1490 | 0.1647 | 0.1686 | 0.1725 | 0.1765 |
| 16 | 0.1373 | 0.1373 | 0.1373 | 0.1412 | 0.1529 | 0.1529 | 0.1569 | 0.1686 |
| 17 | 0.1333 | 0.1333 | 0.1333 | 0.1373 | 0.1373 | 0.1373 | 0.1451 | 0.1569 |
| 18 | 0.1294 | 0.1294 | 0.1294 | 0.1333 | 0.1333 | 0.1373 | 0.1451 | 0.1451 |
| 19 | 0.1373 | 0.1373 | 0.1373 | 0.1373 | 0.1412 | 0.1451 | 0.1451 | 0.1451 |
| 20 | 0.2529 | 0.1490 | 0.1451 | 0.1412 | 0.1412 | 0.1412 | 0.1451 | 0.1490 |
| 21 | 0.1608 | 0.1569 | 0.1608 | 0.1569 | 0.1451 | 0.1451 | 0.1451 | 0.1490 |

Obviously, in Table 1, the brightness component at the position (1, 1) is 0.1725, and the brightness component at the position (2, 1) is 0.1843, and so on.

Figure 3:
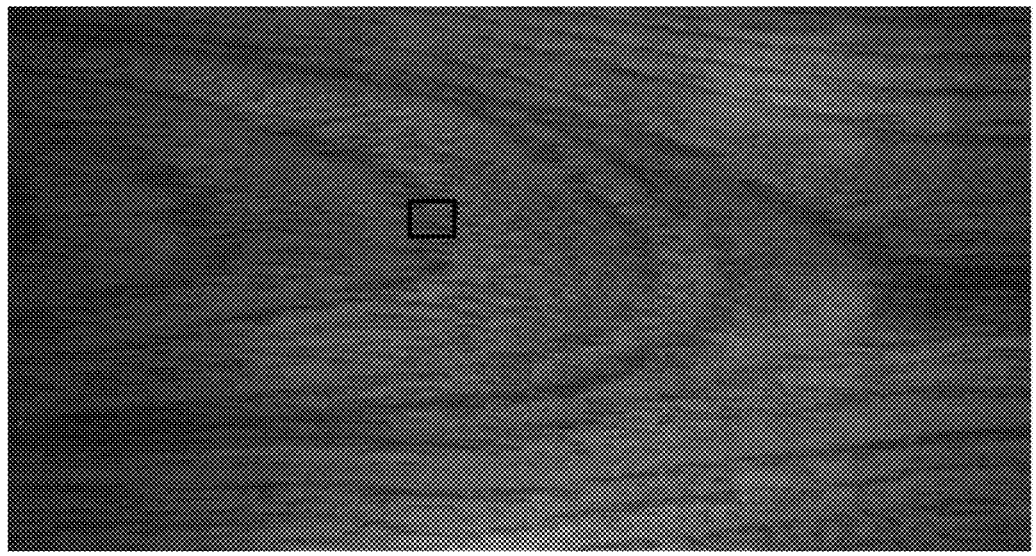
FIG. 3: Schematic image photographed in the diffuse reflected light source based on an embodiment of the present application.

As shown in FIG. 3, the image is photographed under diffuse reflected light sources, and the image only contains the patterns of the trace carrier. Because the image has many matrix elements in a brightness analysis, the analytical results for a selected part of the image are taken for an example as shown in Table 2:

TABLE 2

|    | 1      | 2      | 3      | 4      | 5      | 6      | 7      | 8      |
|----|--------|--------|--------|--------|--------|--------|--------|--------|
| 1  | 0.2510 | 0.2588 | 0.2588 | 0.2510 | 0.2459 | 0.2549 | 0.2431 | 0.2431 |
| 2  | 0.2549 | 0.2627 | 0.2627 | 0.2627 | 0.2706 | 0.2667 | 0.2549 | 0.2510 |
| 3  | 0.2745 | 0.2824 | 0.2706 | 0.2706 | 0.2745 | 0.2706 | 0.2706 | 0.2667 |
| 4  | 0.2863 | 0.2902 | 0.2824 | 0.2824 | 0.2863 | 0.2824 | 0.2863 | 0.2824 |
| 5  | 0.2784 | 0.2824 | 0.1941 | 0.2980 | 0.2941 | 0.2902 | 0.2941 | 0.2902 |
| 6  | 0.2784 | 0.2863 | 0.2980 | 0.3020 | 0.2980 | 0.2980 | 0.3020 | 0.3059 |
| 7  | 0.2902 | 0.2980 | 0.3020 | 0.3059 | 0.3137 | 0.3137 | 0.2980 | 0.3020 |
| 8  | 0.2941 | 0.2980 | 0.3020 | 0.3020 | 0.3098 | 0.3137 | 0.3020 | 0.2941 |
| 9  | 0.2941 | 0.2980 | 0.3020 | 0.2980 | 0.3020 | 0.3098 | 0.3137 | 0.3059 |
| 10 | 0.2863 | 0.2863 | 0.2902 | 0.3059 | 0.3098 | 0.3098 | 0.3137 | 0.3020 |

TABLE 2-continued

|    | 1      | 2      | 3      | 4      | 5      | 6      | 7      | 8      |
|----|--------|--------|--------|--------|--------|--------|--------|--------|
| 11 | 0.2863 | 0.2863 | 0.2784 | 0.2491 | 0.3098 | 0.3098 | 0.3020 | 0.2902 |
| 12 | 0.2745 | 0.2784 | 0.2705 | 0.2706 | 0.2863 | 0.2902 | 0.2784 | 0.2902 |
| 13 | 0.2510 | 0.2549 | 0.2510 | 0.2510 | 0.2510 | 0.2549 | 0.2667 | 0.2784 |
| 14 | 0.2275 | 0.2392 | 0.2353 | 0.2275 | 0.2314 | 0.2431 | 0.2549 | 0.2588 |
| 15 | 0.2118 | 0.2235 | 0.2235 | 0.2157 | 0.2196 | 0.2314 | 0.2393 | 0.2431 |
| 16 | 0.2000 | 0.2078 | 0.2039 | 0.2039 | 0.2078 | 0.2196 | 0.2275 | 0.2314 |
| 17 | 0.1882 | 0.1961 | 0.2000 | 0.2000 | 0.1961 | 0.2039 | 0.2118 | 0.2157 |
| 18 | 0.1922 | 0.1922 | 0.1961 | 0.2000 | 0.1961 | 0.1961 | 0.2039 | 0.2118 |
| 19 | 0.2118 | 0.2078 | 0.2000 | 0.2078 | 0.2039 | 0.2039 | 0.2039 | 0.2118 |
| 20 | 0.2196 | 0.2275 | 0.2196 | 0.2196 | 0.2175 | 0.2039 | 0.2078 | 0.2157 |
| 21 | 0.2196 | 0.2275 | 0.2314 | 0.2314 | 0.2235 | 0.2118 | 0.2118 | 0.2196 |

It is important to note that the intercepted part of the image in FIG. 3 and the intercepted part shown in FIG. 2b are located at the same location in the two images.

Likewise, in Table 2, the brightness component at the position (1, 1) is 0.2510, and the brightness component at the position (2, 1) is 0.2588.

Figure 4:
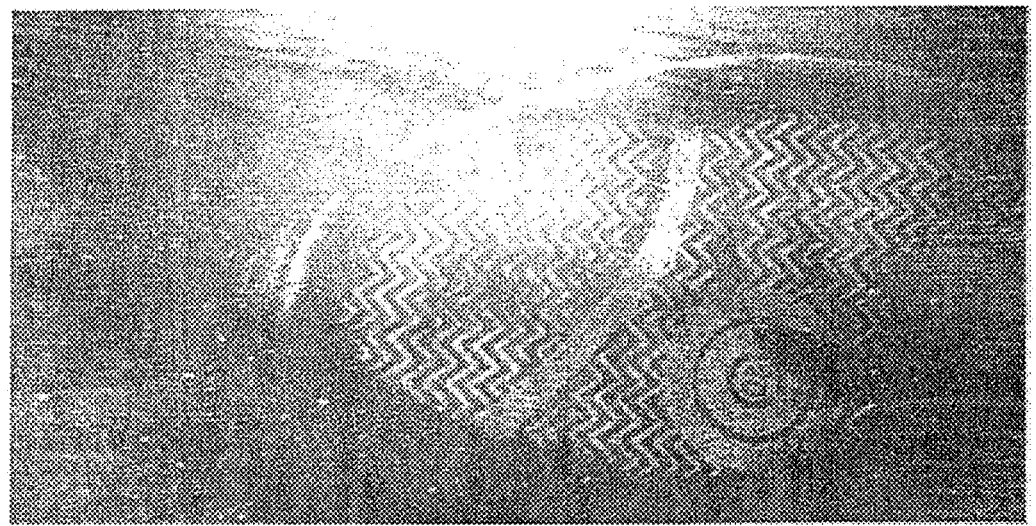
FIG. 4: Schematic image of a footprint without patterns of trace carrier after applying the method of an embodiment of the present application.

As shown in FIG. 4, the image processed through step S105 and S107 is a footprint image without the patterns of the trace carrier. Table 3 shows the division results of the abovementioned two parts after the brightness analysis.

TABLE 3

|    | 1      | 2      | 3      | 4      | 5      | 6      | 7      | 8      |
|----|--------|--------|--------|--------|--------|--------|--------|--------|
| 1  | 0.6875 | 0.7121 | 0.6970 | 0.7031 | 0.7077 | 0.6769 | 0.6935 | 0.6774 |
| 2  | 0.7538 | 0.7015 | 0.7015 | 0.7015 | 0.6957 | 0.6765 | 0.6769 | 0.7031 |
| 3  | 0.7429 | 0.6944 | 0.7391 | 0.7536 | 0.7286 | 0.6957 | 0.6812 | 0.7059 |
| 4  | 0.7260 | 0.7162 | 0.7500 | 0.7361 | 0.7123 | 0.7222 | 0.6986 | 0.6944 |
| 5  | 0.7605 | 0.7500 | 0.7333 | 0.7237 | 0.7200 | 0.7297 | 0.7067 | 0.7027 |
| 6  | 0.7605 | 0.7534 | 0.7500 | 0.7403 | 0.7500 | 0.7500 | 0.7273 | 0.6923 |
| 7  | 0.7568 | 0.7500 | 0.7273 | 0.7308 | 0.7125 | 0.7125 | 0.7368 | 0.7143 |
| 8  | 0.7333 | 0.7237 | 0.7013 | 0.7273 | 0.7215 | 0.7125 | 0.7273 | 0.7333 |
| 9  | 0.6933 | 0.6974 | 0.6753 | 0.7105 | 0.7273 | 0.7089 | 0.7125 | 0.7308 |
| 10 | 0.7260 | 0.7260 | 0.7027 | 0.6923 | 0.7089 | 0.6962 | 0.7000 | 0.7532 |
| 11 | 0.6986 | 0.6986 | 0.7465 | 0.7333 | 0.7089 | 0.6962 | 0.7143 | 0.7703 |
| 12 | 0.7000 | 0.7042 | 0.7536 | 0.7536 | 0.7260 | 0.7162 | 0.7465 | 0.7297 |
| 13 | 0.7031 | 0.7077 | 0.7500 | 0.7500 | 0.7500 | 0.7385 | 0.7059 | 0.6901 |
| 14 | 0.7241 | 0.6885 | 0.7333 | 0.7586 | 0.7458 | 0.7258 | 0.6923 | 0.6970 |
| 15 | 0.7037 | 0.6491 | 0.6667 | 0.6909 | 0.7500 | 0.7288 | 0.7213 | 0.7258 |
| 16 | 0.6863 | 0.6604 | 0.6731 | 0.6923 | 0.7358 | 0.6964 | 0.6897 | 0.7288 |
| 17 | 0.7083 | 0.6800 | 0.6667 | 0.6863 | 0.7000 | 0.6731 | 0.6852 | 0.7273 |
| 18 | 0.6735 | 0.6735 | 0.6600 | 0.6667 | 0.6800 | 0.7000 | 0.7115 | 0.6852 |
| 19 | 0.6481 | 0.6604 | 0.6863 | 0.6604 | 0.6731 | 0.6923 | 0.7115 | 0.6852 |
| 20 | 0.6964 | 0.6552 | 0.6607 | 0.6429 | 0.6545 | 0.6923 | 0.6981 | 0.6909 |
| 21 | 0.7321 | 0.6897 | 0.6949 | 0.6780 | 0.6491 | 0.6852 | 0.6852 | 0.6786 |

Similarly, in Table 3, the brightness component at the position (1, 1) is 0.6875, which is the result of dividing the brightness component at the position (1, 1) in Table 1 by the brightness component at the position (1, 1) in Table 2; the brightness component at the position (2, 1) is 0.7121, which is the result of dividing the brightness component at the position (2, 1) in Table 1 by the brightness component at the position (2, 1) in Table 2. Of course, during the process of calculation, there may be a certain range of errors for some reasons, but those errors have no great impact on the image processing results.

In addition, before the first image's brightness component V1 and the second image's brightness component V2 are obtained, the first image and the second image shall be converted into HSV mode.

Because the footprint extraction method involved in the present application is to photograph a specific area with a fixed camera in different light sources, the corresponding photographing areas of the first image and the second image are the same, which can guarantee the precision of the footprint extraction results, and the improvement of the results is obvious.

Besides, oblique light sources and diffuse reflected light sources alternatively illuminate the photographing area.

Obviously, because the camera photographs different images in oblique light sources and diffuse reflected light sources, the two light sources shall alternatively illuminate the photographing area. Of course, there is no restriction on the sequence of oblique light sources and diffuse reflected light sources' illumination.

Preferred: The intersection angle α between the oblique light and the surface of the trace carrier ranges between $0°\leq\alpha\leq10°$.

Besides, at least two oblique light sources illuminate the photographing area from both sides.

Preferred: The intersection angle β between the diffuse reflector used to form the diffuse reflected light and the trace carrier's surface ranges between $45°<\beta<90°$.

Besides, at least two diffuse reflected light illuminate the photographing area from both sides.

According to the embodiment of the present application, a footprint extraction device is also provided.

As shown in FIG. 5, the device includes:

A first extraction module, is used to photograph a part of or an entire oblique light sources illuminated area to obtain a first image when exposed under said oblique light sources, said first image contains a part of or an entire image of a footprint, and an image of a trace carrier of said footprint;

A second extraction module, is used to photograph a part of or an entire diffuse reflected light sources illuminated area to obtain a second image, said second image contains an image of said trace carrier;

An analysis module, is used to analyze said first image's brightness component V1 and said second image's brightness component V2, and divide said first image's brightness component V1 by said second image's brightness component V2 to produce their brightness distribution ratio V3;

An extraction module, is used to extract a third image corresponding to said brightness distribution ratio V3, said third image only contains said footprint's image.

A conversion module (not shown), is used to convert said first image and said second image into HSV mode, before said first image's brightness component V1 and said second image's brightness component V2 are obtained.

The present application involves a crime scene footprint photography and extraction method and extraction device that can photograph the images of a footprint and its trace carrier using illumination of oblique lights from a fixed angle, and photograph the images of the trace carrier without the footprint in a diffuse reflected light illuminated environment from a fixed angle, and generate two images that can be compared and reduced to obtain the image of the footprint, and then remove the patterns of the footprint's trace carrier, so as to display clear and cognizable a footprint image; Because the two footprint images are photographed from the same angle, they can be processed more accurately. In addition, the on-scene footprint photography and extraction method provided in this application is simple and effective, and the footprint's image can be obtained rapidly.

The forgoing description disclosed a better embodiment of the present application; however, the application is not restricted by the embodiment. Any technician who is familiar with the art can make possible changes and modifications to the technical scheme of this application by using the abovementioned method and technical content, or change into the equivalent cases, without exceeding the scope of the present application's technical scheme. Therefore, any simple modification, or equivalent change and modification based on the technical essence of the present application falls within the present application's protection scope, as long as the modifications or changes do not exceed the content of the present application's technical scheme.

The invention claimed is:

1. A method for photographing and extracting crime scene footprint images including the following steps:
    S1: Exposing under an oblique light source, and photographing a part of or an entire illuminated area of said oblique light source from a fixed angle to obtain a first image, said first image contains a part of or an entire image of a footprint and a trace carrier image of said footprint;
    S2: Exposing under a diffuse reflected light source, and photographing a part of or an entire illuminated area of said diffuse reflected light source from a fixed angle to obtain a second image, said second image contains an image of said trace carrier without any footprints;
    S3: Analyzing said first image's brightness component V1 and said second image's brightness component V2, and divide said first image's brightness component V1 by said second image's brightness component V2 to produce their brightness distribution ratio V3;
    S4: Extracting a third image corresponding to said brightness distribution ratio V3, said third image only contains an image of said footprint.

2. A method according to claim 1, wherein before said first image's brightness component V1 and said second image's brightness component V2 are obtained, converting said first image and said second image into HSV mode.

3. A method according to claim 1, wherein in an oblique light illuminating environment, the intersection angle α between said oblique light and said footprint's trace carrier ranges between $0°≤α≤10°$.

4. A method according to claim 1, wherein said first image and said second image share the same photographing area.

5. A method according to claim 1, wherein said oblique light is formed from at least two light sources located on both sides along said footprint's width direction, said oblique light sources' length direction is consistent with said footprint's length direction; said oblique light sources can compensate each other to illuminate entire said footprint.

6. A method according to claim 5, wherein said oblique light sources that form said oblique light, are formed in a strip structure.

7. A method according to claim 6, wherein said oblique light sources that form said oblique light, are formed with collimating lens or the collimating lens system.

8. A method according to claim 1, wherein in said diffuse reflected light source illuminating environment, said diffuse reflected light is emitted by area light sources, said diffuse reflected light is formed from at least two said area light sources, said two area light sources are located on both sides of said footprint's width direction and said two area light sources' length direction is consistent with said footprint's length direction.

9. A method according to claim 8, wherein said oblique light source and said diffuse reflected light source alternatively illuminate a photographing area.

10. A method according to claim 8, wherein said oblique light sources and said diffuse reflected light sources are formed from white light sources.

11. A method according to claim 8, wherein said intersection angle β between a diffuse reflector used to form said diffuse reflected light and said trace carrier's surface ranges between $45°≤β≤90°$.

* * * * *